(12) United States Patent
Parker et al.

(10) Patent No.: US 9,024,080 B2
(45) Date of Patent: *May 5, 2015

(54) PROCESS FOR ISOLATING CRYSTALLIZED 2,2,4,4 TETRAMETHYL-1,3-CYCLOBUTANEDIOL (TMCD) PARTICLES UTILIZING PRESSURE FILTRATION

(71) Applicant: Eastman Chemical Company, Kingsport, TN (US)

(72) Inventors: Kenny Parker, Afton, TN (US); Craig Hoyme, Fall Branch, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/486,054

(22) Filed: Sep. 15, 2014

(65) Prior Publication Data

US 2014/0378716 A1    Dec. 25, 2014

Related U.S. Application Data

(63) Continuation of application No. 13/330,052, filed on Dec. 19, 2011, now Pat. No. 8,859,825.

(60) Provisional application No. 61/425,286, filed on Dec. 21, 2010.

(51) Int. Cl.
*C07C 35/04* (2006.01)
*C07C 29/76* (2006.01)

(52) U.S. Cl.
CPC ............. *C07C 29/76* (2013.01); *C07C 2101/04* (2013.01); *C07C 35/045* (2013.01)

(58) Field of Classification Search
CPC .................................................. C07C 2101/04
USPC ......................................................... 568/839
See application file for complete search history.

(56) References Cited

U.S. PATENT DOCUMENTS

| 5,169,994 A | 12/1992 | Sumner, Jr. et al. |
| 5,258,556 A | 11/1993 | Sumner, Jr. et al. |
| 7,989,667 B2 | 8/2011 | O'meadhra |
| 8,859,825 B2 * | 10/2014 | Parker et al. ................ 568/839 |

OTHER PUBLICATIONS

USPTO Notice of Allowance dated Jul. 7, 2014 for copending U.S. Appl. No. 13/330,052.

* cited by examiner

*Primary Examiner* — Sudhakar Katakam
(74) *Attorney, Agent, or Firm* — Steven A. Owen

(57) ABSTRACT

A method for isolating 2,2,4,4-tetramethyl-1,3-cyclobutanediol (TMCD) solids from an isolated feed slurry formed in a TMCD process comprising TMCD, a liquid phase, and impurities by (a) treating the isolated feed slurry in a product isolation zone to produce an isolated TMCD product wet cake, a mother liquor, and impurities; wherein the product isolation zone can comprise at least one rotary pressure drum filter.

5 Claims, 3 Drawing Sheets

US 9,024,080 B2

Figure 1:
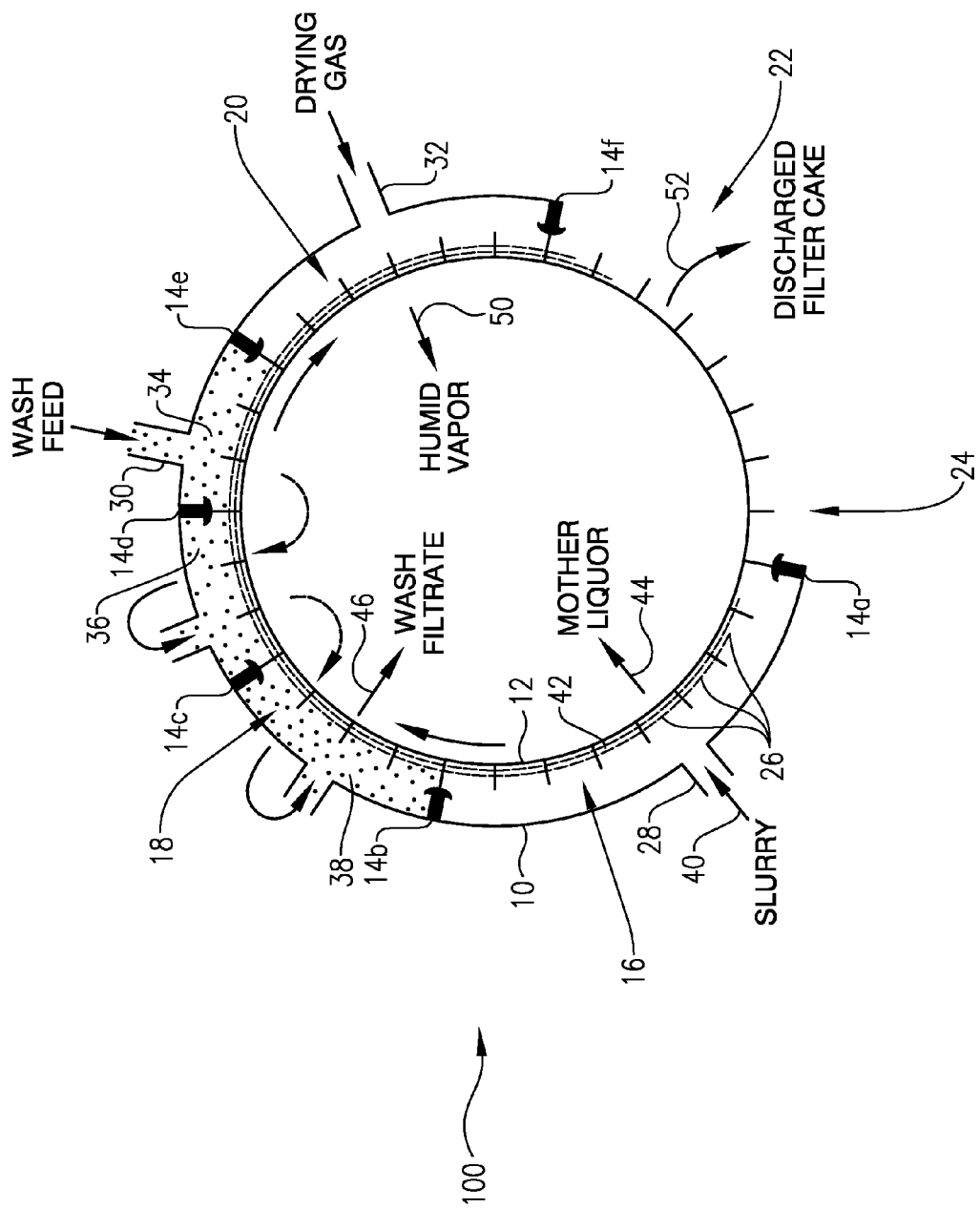

PROCESS FOR ISOLATING CRYSTALLIZED 2,2,4,4 TETRAMETHYL-1,3-CYCLOBUTANEDIOL (TMCD) PARTICLES UTILIZING PRESSURE FILTRATION

CROSS-REFERENCE TO RELATED APPLICATIONS

This application is a continuation of U.S. application Ser. No. 13/330,052, filed Dec. 19, 2011 which claims priority to U.S. Provisional Application Ser. No. 61/425,286, filed Dec. 21, 2010, the disclosure of which is incorporated herein by reference in its entirety.

FIELD OF THE INVENTION

The present invention relates generally to a product isolation process for use in 2,2,4,4-tetramethyl-1,3-cyclobutanediol (TMCD) production processes. More specifically, the present invention concerns equipment and processes for isolating crystallized 2,2,4,4-tetramethyl-1,3-cyclobutanediol (TMCD) particles from a slurry comprising TMCD, a liquid phase, and TMCD reaction byproduct impurities.

BACKGROUND OF THE INVENTION

The problem to be solved is how to isolate TMCD solids from a crystallized slurry and wash the solids to reduce the mother liquor content when there is much variability in the particle size distribution. Variability in the particle size distribution impacts the filtration rate, cake washing, and the tendency for filter cloth fouling. Solid TMCD particles can range from sub micron to greater than 1000 microns. Filtration is not a predictive discipline. It is necessary to discover what the acceptable cake height is, wash ratio, and cloth wash methods for minimizing fouling, and acceptable filtration rates for the given characteristics of the slurry to be filtered. There is a need in the industry to discover a solid liquid separation technology capable of isolating TMCD solids from a TMCD slurry.

SUMMARY OF THE INVENTION

In one embodiment of the invention, a process for isolating crystallized 2,2,4,4-tetramethyl-1,3-cyclobutanediol (TMCD) particles is provided comprising treating an isolation feed slurry comprising the 2,2,4,4-tetramethyl-1,3-cyclobutanediol (TMCD) particles in a product isolation zone to produce an isolated TMCD product wet cake comprising the 2,2,4,4-tetramethyl-1,3-cyclobutanediol (TMCD) in an amount of at least 65 weight percent, wherein the product isolation zone 100 is defined as a rotary pressure drum filter.

In another embodiment of the invention, a process for isolating crystallized 2,2,4,4-tetramethyl-1,3-cyclobutanediol (TMCD) particles is provided comprising:
(a) introducing an isolation feed slurry comprising the TMCD particles and a liquid phase into a product isolation zone; wherein the product isolation zone comprises a rotary pressure drum filter;
(b) removing at least a portion of the liquid phase to produce an isolated TMCD product wet cake and a mother liquor stream; and
(c) routing at least a portion of the mother liquor to a solvent recovery zone.

In another embodiment of the invention, a process for isolating crystallized 2,2,4,4-tetramethyl-1,3-cyclobutanediol (TMCD) particles is provided comprising:
(a) introducing an isolation feed slurry comprising the TMCD particles and a liquid phase into a product isolation zone; wherein the product isolation zone comprises a rotary pressure drum filter.
(b) removing at least a portion of the liquid phase to produce an isolated TMCD product wet cake and a mother liquor stream; and
(c) routing at least a portion of the mother liquor stream to a solvent recovery zone to generate a recycle mother liquor stream and TMCD reaction by-product impurity rich stream enriched in TMCD reaction by-products, and
(d) routing at least a portion of TMCD reaction by-product impurity rich stream enriched with TMCD reaction by-products to a purge zone.

In another embodiment of the invention, a process for isolating crystallized 2,2,4,4-tetramethyl-1,3-cyclobutanediol (TMCD) particles is provided comprising:
(a) introducing an isolation feed slurry comprising the TMCD particles and a liquid phase into a product isolation zone;
(b) removing at least a portion of the liquid phase to thereby produce an isolated TMCD product wet cake and a mother liquor stream; and
(c) routing at least a portion of the isolated TMCD product wet cake to a dryer; and
(d) routing at least a portion of the mother liquor stream to a solvent recovery zone to generate a recycle mother liquor stream and a TMCD reaction by-product impurity rich stream enriched in TMCD reaction by-products, and
(e) routing at least a portion of the TMCD reaction by-product impurity rich stream enriched with TMCD reaction by-products to purge zone, wherein the product isolation zone comprises a rotary pressure drum filter.

In yet another embodiment of the invention, a process for isolating crystallized 2,2,4,4-tetramethyl-1,3-cyclobutanediol (TMCD) particles is provided comprising:
(a) introducing an isolation feed slurry comprising the TMCD particles and a liquid phase into a product isolation zone;
(b) removing at least a portion of the liquid phase to thereby produce an isolated TMCD product wet cake and a mother liquor stream; and
(c) routing at least a portion of the isolated TMCD wet cake to a dryer;
(d) routing at least a portion of the mother liquor stream to a solvent recovery zone to generate a recycle mother liquor stream and TMCD reaction by-product impurity rich stream enriched in TMCD reaction by products, and
(e) routing at least a portion of the mother liquor stream to a purge zone, wherein the product isolation zone is defined within a rotary pressure drum filter.

BRIEF DESCRIPTION OF THE DRAWING FIGURES

Preferred embodiments of the present invention is described in detail below with reference to the attached drawing figures, wherein:
FIG. 1 is a schematic representation of a rotary pressure drum filter that can be employed to isolate 2,2,4,4-tetramethyl-1,3-cyclobutanediol (TMCD) from the liquid phase of a isolation feed slurry produced in a TMCD process.

Figure 2:
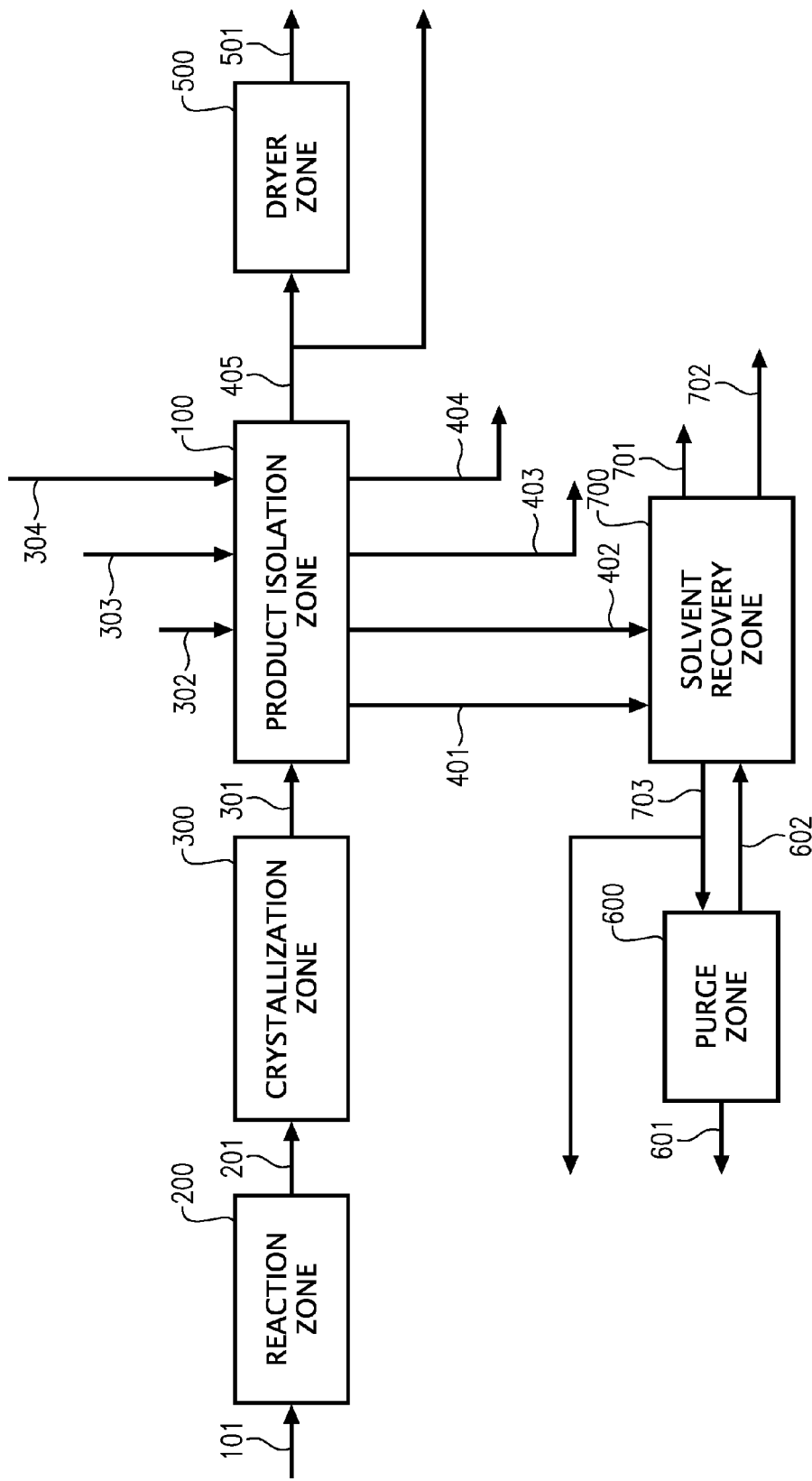

FIG. 2 is a process flow diagram illustrating one embodiment for the production of TMCD particles, particularly illustrating a configuration comprising the following steps: 1) TMCD particles are produced in a reaction zone 200, 2) crystalline TMCD solids are formed in crystallization zone 300, 3) the resulting TMCD isolation feed slurry stream 301 is routed to the product isolation zone 100 to generate an isolated TMCD product wet cake stream 405, a mother liquor stream 401, and a wash liquor stream 402. Up to 100% of the isolated TMCD product wet cake stream 405 can be directed to dryer zone 500 or exit the process as a wet cake. Mother liquor stream 401 and wash liquor stream 402 are routed to a solvent recovery zone 700 to produce a recycle mother liquor stream 701, a recycle cake wash stream 702, and a TMCD reaction by-product impurity rich stream 703. A portion of the TMCD reaction by-product impurity rich stream 703 can be routed to a purge zone 600 to produce purge stream 601 that exits the process.

Figure 3:
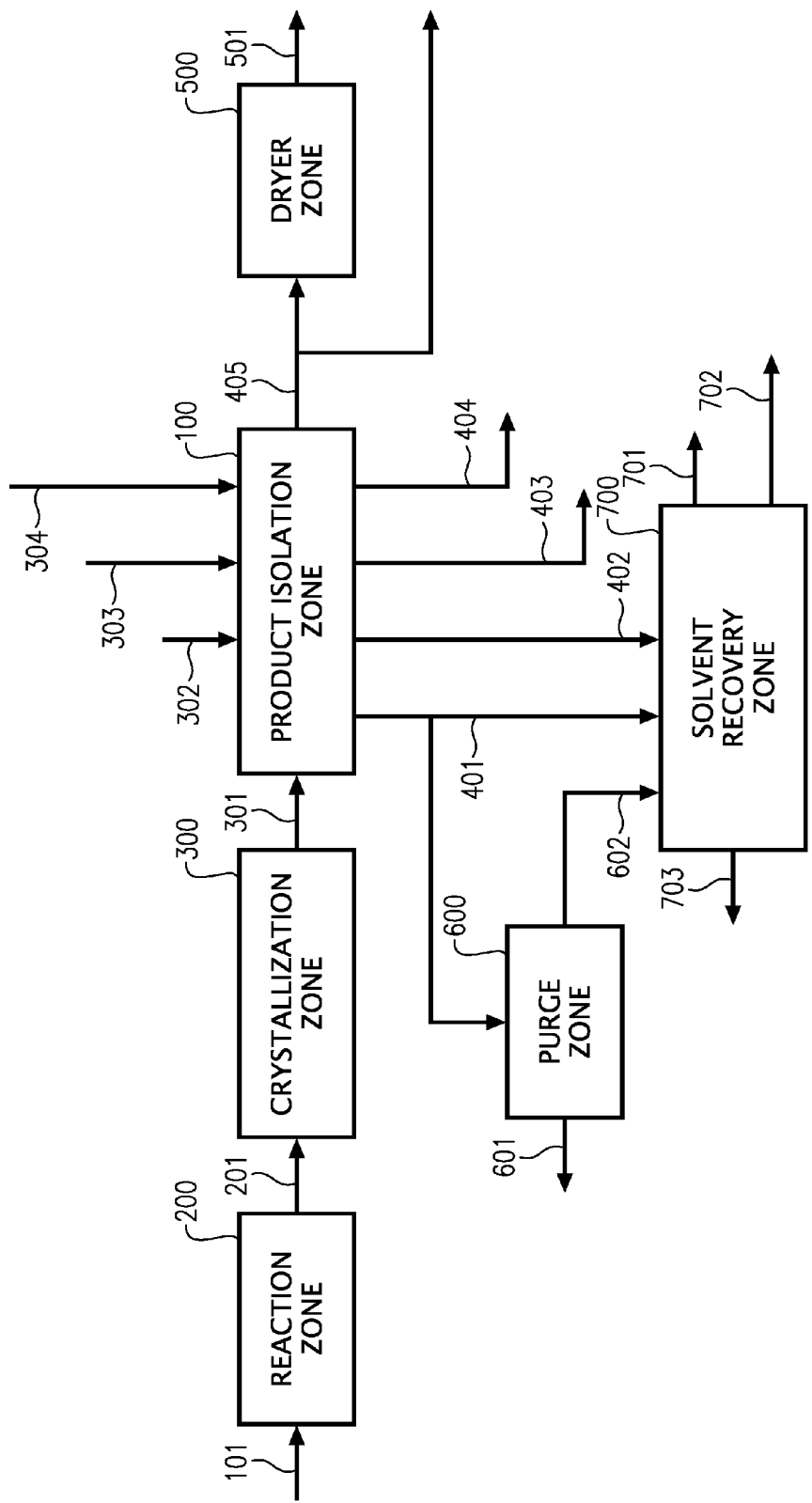

FIG. 3 is a process flow diagram illustrating another embodiment for the production of TMCD comprising the following steps: 1) the TMCD is produced in a reaction zone 200, 2) crystalline TMCD solids are formed in crystallization zone 300, and 3) the resulting TMCD isolation feed slurry stream 301 is routed to the product isolation zone 100 to generate an isolated TMCD product wet cake stream 405, a mother liquor stream 401, and a wash liquor stream 402. Up to 100% of the isolated TMCD product wet cake 405 can be directed to dryer zone 500 or exit the process as a wet cake. At least a portion of mother liquor stream 401 and wash liquor stream 402 are routed to a solvent recovery zone 700 to produce a recycle mother liquor stream 701, a recycle cake wash stream 702, and a TMCD reaction by-product impurity rich stream 703. At least a portion of mother liquor stream 401 is routed to purge zone 600 to produce a purge stream 601.

DETAILED DESCRIPTION

In accordance with one embodiment of the present invention, an isolation feed slurry stream 301 comprising 2,2,4,4-tetramethyl-1,3-cyclobutanediol (TMCD) solids, a mother liquor, and TMCD reaction by-product impurities can be treated in a product isolation zone 100. The product isolation zone 100 can separate the isolation feed slurry stream 301 into a primarily fluid phase mother liquor and a primarily solid phase isolated TMCD product wet cake comprising isolated TMCD solids.

In one embodiment of the present invention, a product isolation zone 100 of a 2,2,4,4-tetramethyl-1,3-cyclobutanediol (TMCD) production process comprises a rotary pressure drum filter, similar to the device depicted in FIG. 1. In one embodiment, the product isolation zone 100 can be a mother liquor and impurity removal zone comprising a rotary pressure filter. As used herein, the term "rotary pressure drum filter" denotes a device that uses a pressure differential across a rotating drum filter to facilitate solid/liquid separation. The rotary pressure drum filter depicted in FIG. 1 comprises a housing 10 and a rotary drum filter 12 rotatably disposed within housing 10. An annulus is defined between the inside of housing 10 and the outside of rotary drum filter 12. This annulus is divided into various discreet zones by seals 14a, b, c, d, e, f. A filtration zone 16 can be defined in the annulus between seals 14a and 14b. A wash zone 18 can be defined in the annulus between seals 14b and 14e. A dewatering/drying zone 20 can be defined in the annulus between seals 14e and 14f. Housing 10 can be open between seals 14f and 14a. This open portion of housing 10 can include a discharge zone 22 and a cloth wash zone 24.

Referring still to FIG. 1, rotary drum filter 12 can define a plurality of filter cells 26 located on the periphery of the drum. The bottom of each filter cell 26 is formed of a filter media (e.g., synthetic cloth, single-layer metal cloth, or multi-layer metal cloth). Fluid flow through the filter media can be caused by creating a pressure differential across the filter media. Each filter cell 26 has its own outlet for discharging fluids inwardly towards the axis of rotation of rotary drum filter 12. The outlets of axially-aligned filter cells 26 are manifolded. The manifolds (not shown) rotate with the rotary drum filter 12 and communicate with a service/control head (not shown) which collects the fluids from the manifolds in a manner that allows the fluids discharged from zones 16, 18, and 20 to be kept separate.

Housing 10 can define an isolation feed slurry inlet 28 that can communicate with filtration zone 16, a wash feed inlet 30 that can communicate with wash zone 18, and a drying gas inlet 32 that can communicate with dewatering/drying zone 20. Wash zone 18 can be divided into an initial wash zone 34, an intermediate wash zone 36, and a final wash zone 38 by seals 14c and 14d. Housing 10 and rotary drum filter 12 can be configured to permit filtrate discharged from initial wash zone 34 to enter intermediate wash zone 36, and filtrate discharged from intermediate wash zone 36 to enter final wash zone 38.

In operation, an isolation feed slurry in line 301 can enter filtration zone 16 via slurry inlet 28. The isolation feed slurry in line 301 can comprise TMCD, a liquid phase, and TMCD reaction byproduct impurities. In one embodiment, the isolation feed slurry in line 301 can comprise 2,2,4,4-tetramethyl-1,3-cyclobutanediol (TMCD) in an amount of at least about 5 weight percent, at least about 20 weight percent, or at least 50 weight percent.

In one embodiment, the isolation feed slurry can comprise solid TMCD particles in an amount in the range of from about 1 to about 60 weight percent, in the range of from about 5 to about 45 weight percent, or in the range of from 15 to 35 weight percent. The solid TMCD particles in the isolation feed slurry can have a particle size ranging from less than 1 micron to at least 1000 microns with a mean particle size in the range of from about 50 to about 600 microns, or in the range of from 100 to 450 microns. In one embodiment, the isolated TMCD product wet cake 405 can have an average concentration of at least about 65 weight percent TMCD solids, at least about 85 weight percent TMCD solids, or at least 95 weight percent TMCD solids.

The isolation feed slurry introduced into filtration zone 16 can form a filter cake (i.e., a wet cake) 42 in filter cells 26 on the periphery of rotary filter drum 12. In filtration zone 16, predominately fluid phase mother liquor can be discharged radially inward from the bottom of each filter cell 26. The mother liquor collected from filtration zone 16 can be discharged from the apparatus via line 401. Upon obtaining a desired height of filter cake 42 in filtration zone 16, rotary drum filter 12 can rotate so that filter cake 42 enters wash zone 18.

In wash zone 18, filter cake 42 can be washed with a wash feed entering initial wash zone 34 via wash feed inlet 30. The wash feed comprises any liquid capable of displacing mother liquor in a wash zone with a TMCD solubility less than 35 g TMCD/100 g liquid wash feed at the wash temperature, preferably less than 10 g TMCD/100 g liquid wash feed at the wash temperature, more preferably less than 5 g TMCD/100 g liquid wash feed at the wash temperature, and most preferably less than 1 g TMCD/100 g liquid wash feed at the wash temperature.

Furthermore, the wash feed can have a temperature in the range of from about the freezing point of the wash feed to about the boiling point of the wash feed, in the range of from about 1° C. to about 100° C., or in the range of from 1° C. to 50° C., or in the range from 3° C. to 35° C. In another embodiment, the wash feed temperature can range from about −30° C. to about 75° C., from about −20° C. to about 50° C., or from about −10° C. to about 35° C. The total amount of wash feed routed to wash zone 18 is defined as the wash ratio and is defined as the mass of wash divided by the mass of filter cake solids. The wash ratio can range from 0.4 to 5.0, more preferably can range from 0.5 to 3.0, and most preferably can range from 0.5 to 2.0. Wash liquor from initial wash zone 34 can then be transferred to intermediate wash zone 36, and the wash filtrate from intermediate wash zone 36 can then be transferred to final wash zone 38. The wash filtrate (i.e., wash liquor) stream can then be discharged from product isolation zone 100 via line 402. In one embodiment of the present invention, only two wash zones 36 and 38 exist in the filter. In another embodiment of the present invention only one wash zone 38 exists in the filter.

In one embodiment of the present invention, the wash filtrate in line 402 can be combined into the mother liquor in line 401. In another embodiment the wash filtrate in line 402 and mother liquor in line 401 are routed to different locations. After suitable washing in wash zone 18, rotary drum filter 12 can rotate so that washed filter cake 42 can enter dewatering/drying zone 20.

In dewatering/drying zone 20, liquid can be removed from washed filter cake 42 by passing a dewatering gas, entering via gas inlet 32, through washed filter cake 42 to displace free mobile liquid. The dewatering gas introduced into inlet 32 can comprise nitrogen, carbon dioxide. Liquid removed from washed filter cake 42 can exit product isolation zone 100 via line 50, and can exit in a liquid phase and/or a vapor phase. Additionally, the gas stream passed through washed filter cake 42 can exit product isolation zone 100 as a humid vapor via line 50. After filter cake 42 is dewatered/dried in zone 20, rotary drum filter 12 can rotate so that dried filter cake 42 enters discharge zone 22.

In discharge zone 22, at least a portion of filter cake 42 can be disengaged from rotary drum filter 12 and can exit product isolation zone 100 via line 405. In one embodiment, discharge of isolated TMCD product wet cake stream 405 from a solid liquid separation device in the product isolation zone 100 comprises routing a gas stream through the solid liquid separation device into the isolated TMCD product wet cake wherein the gas blows out at least a portion of the isolated TMCD product wet cake 405 out of the solid liquid separation device.

In another embodiment, discharge of isolated TMCD product wet cake 405 from a solid liquid separation device in product isolation zone 100 comprises routing a liquid stream through the solid liquid separation device into the isolated TMCD product wet cake where in the liquid stream causes at least a portion of isolated TMCD product wet cake 405 to exit the solid liquid separation device.

In another embodiment, discharge of isolated TMCD product wet cake 405 from a solid liquid separation device in product isolation zone 100 comprises routing a liquid directly into the isolated TMCD product wet cake contained in the discharge zone of the solid liquid separation device thus washing out at least a portion of the solids from the solid liquid separation device resulting in a stream 405 comprising a slurry having a weight % TMCD greater than 10 weight %, greater than 25%, greater than 35 weight %.

In yet another embodiment, discharge of the isolated TMCD product wet cake stream 405 from a solid liquid separation device in product isolation zone 100 comprises routing a gas stream mixed with a liquid stream through the solid liquid separation device into the solid liquid separation device wherein the gas blows out at least a portion of the isolated TMCD product wet cake stream 405 out of the solid liquid separation device.

Rotary drum filter 12 can then rotate into cloth wash zone 24, where any solid particles remaining in filter cells 26 can be removed.

In one embodiment, isolated TMCD product wet cake 42 discharged via line 405 can comprise at least about 10 weight percent of the above-mentioned TMCD. Furthermore, the isolated TMCD product wet cake in line 405 can comprise the above-mentioned solid TMCD particles in an amount in the range of from about 70 to about 95 weight percent, in the range of from about 75 to about 90 weight percent, or in the range of from 77 to 88 weight percent.

An example of a suitable commercially available rotary pressure drum filter which can be employed in product isolation zone 100 includes, but is not limited to, a BHS-FEST ROTARY PRESSURE FILTER, available from BHS-Sonthofen GmbH, D-87527, Sonthofen, Germany.

FIG. 2 illustrates one embodiment of the present invention where the product isolation device discussed above with reference to FIG. 1 can be employed in a TMCD production process where TMCD produced in reaction zone 200, crystallized in crystallization zone 300, then subjected to product isolation in product isolation zone 100. Isolated feed slurry stream 301, wash feed stream 302, dewater displacement gas stream 303, and cloth wash stream 304 are routed to product isolation zone 100 to produce an isolated TMCD product wet cake stream 405, a mother liquor stream 401, and a wash liquor stream 402, a humid vapor stream 403, and a cloth wash liquor stream 404.

The isolated TMCD product wet cake stream 405 can be routed in whole or in part to dryer zone 500 to produce a TMCD powder stream 501. Alternatively, the dryer zone 500 can be bypassed entirely resulting in isolated TMCD product wet cake stream 405 exiting the TMCD process. The moisture content of stream 501 can be less than 25%, less than 10%, less than 3%, or less than 1%.

The cloth wash liquor stream 404 can be routed and combined with wash feed stream 302 to capture any solids in the cloth wash liquor stream 404 in the isolated TMCD product wet cake. In another embodiment, the cloth wash liquor stream 404 is not combined with the wash feed stream 302. At least a portion of mother liquor stream 401 and at least a portion of the wash liquor stream 402 can be routed to a solvent recovery zone 700 wherein the solvent recovery zone comprises at least one evaporative unit and/or at least one membrane unit to produce recycle mother liquor stream 701, a recycle cake wash feed stream 702, and TMCD reaction by-products enriched stream 703 wherein the concentration of TMCD reaction by-products is greater in stream 703 than stream 401. At least a portion of the recycle wash liquor stream 702 can be routed to the wash feed stream 302. At least a portion of the recycle mother liquor stream 701 can be routed to a location upstream of the product isolation zone 100. At least a portion of TMCD reaction by-products enriched stream 703 can be routed to purge zone 600 to produce a purge stream 601 and a solvent recycle stream 602 which can be routed to solvent recovery zone 700.

In another embodiment, the product isolation zone 100 comprises at least one solid liquid separation device. Solid liquid separation devices are any known in the art capable of dewatering the TMCD solids, including, but not limited to, rotary pressure drum filters.

In one embodiment, the isolation feed slurry stream 301 can comprise solid TMCD particles in an amount in the range of from about 1 to about 60 weight percent, in the range of from about 5 to about 45 weight percent, or in the range of from 15 to 35 weight percent. The solid TMCD particles in the isolation feed slurry stream 301 can have a particle size ranging from less than 1 micron to at least 1000 microns with a mean particle size ranging from about 50 to about 600 microns, or in the range of from 100 to 450 microns. In one embodiment, the isolated TMCD product wet cake 405 can have an average concentration of at least about 65 weight percent TMCD solids, at least about 85 weight percent TMCD solids, or at least 95 weight percent TMCD solids.

The wash feed stream 302 comprises any liquid capable of displacing a portion of the liquid phase from the isolation feed slurry in the product isolation zone. The wash stream 302 can comprise a liquid with a TMCD solubility less than 35 g TMCD/100 g liquid wash feed at the wash temperature, less than 10 g TMCD/100 g liquid wash feed at the wash temperature, less than 5 g TMCD/100 g liquid wash feed at the wash temperature, or less than 1 g TMCD/100 g liquid wash feed at the wash temperature.

Furthermore, the wash feed stream 302 can have a temperature in the range of from about the freezing point of the wash feed stream to about the boiling point of the wash feed stream, in the range of from about 1° C. to about 100° C., or in the range of from 1° C. to 50° C., or in the range from 3° C. to 35° C.

The total amount of the wash feed stream routed to the product isolation zone 100 is defined as the wash ratio and is defined as the mass of wash divided by the mass of filter cake solids. The wash ratio can range from about 0.4 to about 5.0, from about 0.5 to about 3.0, or from 0.5 to 2.0.

In another embodiment, the dewatering gas stream 303 can be any gas inert to oxidation reactions. In another embodiment, the dewatering gas stream 303 introduced to product isolation zone 100 comprises nitrogen. In another embodiment, the dewatering gas stream 303 comprises carbon dioxide. In one embodiment, discharge of isolated TMCD product wet cake 405 from a solid liquid separation device in the product isolation zone 100 comprises routing a gas stream through the solid liquid separation device into the isolated TMCD product wet cake wherein the gas blows out at least a portion of the isolated TMCD product wet cake stream 405 out of the solid liquid separation device.

In another embodiment, discharge of isolated TMCD product wet cake 405 from a solid liquid separation device in the product isolation zone 100 comprises routing a liquid stream through the solid liquid separation device into the isolated TMCD product wet cake where in the liquid stream causes at least a portion of the isolated TMCD product wet cake 405 to exit the solid liquid separation device.

In another embodiment, discharge of isolated TMCD product wet cake 405 from a solid liquid separation device in product isolation zone 100 comprises routing a liquid directly into the isolated TMCD product wet cake contained in the discharge zone of the solid liquid separation device thus washing out at least a portion of the isolated TMCD product wet cake from the solid liquid separation device resulting in a stream 405 comprising a slurry having a weight % TMCD greater than 10 weight %, greater than 25%, or greater than 35 weight %.

In yet another embodiment, discharge of isolated TMCD product wet cake 405 from a solid liquid separation device in the product isolation zone 100 comprises routing a gas stream mixed with a liquid stream through the solid liquid separation device into the isolated TMCD product wet cake where in the gas blows out at least a portion of isolated TMCD product wet cake stream 405 out of the solid liquid separation device. The cloth wash stream 304 can be any solvent suitable for removing TMCD solids from the solid liquid separation device. In one embodiment, cloth wash stream 304 comprises mother liquor. In another embodiment, the cloth wash stream 304 comprises a solvent capable of dissolving a portion of TMCD solids from the solid liquid separation device with the residence time of the wash zone. The cloth wash feed 304 is routed to the solid liquid separation device via a pressurized spray nozzle system where in the pressure of cloth wash stream 304 fed to the spray nozzles is greater than 25 psi gauge, greater than 50 psi gauge, greater than 100 psi, greater than 150 psi gauge, or greater than 250 psi gauge. The temperature of cloth wash stream 304 is controlled to prevent more than 10% of the stream flashing at the exit of the high pressure spray nozzles.

FIG. 3 illustrates another embodiment of the present invention where the product isolation device discussed above with reference to FIG. 1 can be employed in a TMCD production process where TMCD is produced in reaction zone 200, crystallized in crystallization zone 300, then subjected to product isolation in product isolation zone 100. Isolated feed slurry stream 301, wash feed stream 302, dewater displacement gas stream 303, and cloth wash stream 304 can be routed to product isolation zone 100 to produce an isolated TMCD product wet cake 405, a mother liquor stream 401, a wash liquor stream 402, a humid vapor stream 403, and a cloth wash liquor stream 404. The isolated TMCD product wet cake stream 405 can be routed in whole or in part to dryer zone 500 to produce a TMCD powder stream 501. Alternatively, the dryer zone 500 can be bypassed entirely resulting in isolated TMCD product wet cake stream 405 exiting the TMCD process. The moisture content of stream 501 can be less than 25%, less than 10%, less than 3% or less than 1%.

The cloth wash liquor stream 404 can be routed and combined with wash feed stream 302 to capture any solids in cloth wash liquor stream 404 in the isolated TMCD product wet cake. In another embodiment, the cloth wash liquor stream 404 is not combined with the wash feed stream 302. At least a portion of mother liquor stream 401 and at least a portion of wash liquor stream 402 can be routed to a solvent recover zone 700 wherein the solvent recovery zone comprises at least one evaporative unit operation and/or at least one membrane unit operation to produce a recycle mother liquor stream 701, a recycle cake wash feed stream 702, and a TMCD reaction by-products enriched stream 703 wherein the concentration of TMCD reaction by-products is greater in stream 703 than stream 401. At least a portion of recycle wash liquor stream 702 can be routed to the wash feed stream 302. At least a portion of the recycle mother liquor stream 701 can be routed to a location upstream of the product isolation zone 100. At least a portion of mother liquor stream 401 can be routed to purge zone 600 to produce a purge stream 601 and a solvent recycle stream 602, which can be routed to the solvent recovery zone 700.

In another embodiment, the product isolation zone 100 comprises at least one solid liquid separation device. Solid liquid separation devices were previously discussed in this disclosure.

That which is claimed is:

1. A process for isolating crystallized 2,2,4,4-tetramethyl-1,3-cyclobutanediol (TMCD) particles comprising:
treating an isolation feed slurry comprising the 2,2,4,4-tetramethyl-1,3-cyclobutanediol (TMCD) particles in a product isolation zone to produce an isolated TMCD product wet cake comprising the 2,2,4,4-tetramethyl-1, 3-cyclobutanediol (TMCD) in an amount of at least 65 weight percent, wherein the product isolation zone is defined as a rotary pressure drum filter having a wash ratio ranging from 0.4 to 5.0;

wherein said TMCD particles comprise 5% to 45% weight percent solids in the feed slurry; and wherein said feed slurry have a mean particle size ranging from less than 50 microns to about 600 microns.

2. A process for isolating crystallized 2,2,4,4-tetramethyl-1,3-cyclobutanediol (TMCD) particles comprising:
   (a) introducing an isolation feed slurry comprising the TMCD particles and a liquid phase into a product isolation zone; wherein the product isolation zone comprises a rotary pressure drum filter having a wash ratio ranging from 0.4 to 5.0;
   (b) removing at least a portion of the liquid phase to produce an isolated TMCD product wet cake and a mother liquor stream; and
   (c) routing at least a portion of the mother liquor to a solvent recovery zone wherein said TMCD particles comprise 5% to 45% weight percent solids in the feed slurry; and wherein said feed slurry have a mean particle size ranging from less than 50 microns to about 600 microns.

3. A process for isolating crystallized 2,2,4,4-tetramethyl-1,3-cyclobutanediol (TMCD) particles comprising:
   (a) introducing an isolation feed slurry comprising the TMCD particles and a liquid phase into a product isolation zone; wherein the product isolation zone comprises a rotary pressure drum filter having a wash ratio ranging from 0.4 to 5.0;
   (b) removing at least a portion of the liquid phase to thereby produce an isolated TMCD product wet cake and a mother liquor stream; and
   (c) routing at least a portion of the mother liquor stream to a solvent recovery zone to generate a recycle mother liquor stream and TMCD reaction by-product impurity rich stream enriched in TMCD reaction by-products, and
   (d) routing at least a portion of TMCD reaction by-product impurity rich stream enriched with TMCD reaction by-products to a purge zone; and wherein said TMCD particles comprise 5% to 45% weight percent solids in the feed slurry; and wherein said feed slurry have a mean particle size ranging from less than 50 microns to about 600 microns.

4. A process for isolating crystallized 2,2,4,4-tetramethyl-1,3-cyclobutanediol (TMCD) particles comprising:
   (a) introducing an isolation feed slurry comprising the TMCD particles and a liquid phase into a product isolation zone;
   (b) removing at least a portion of the liquid phase to thereby produce an isolated TMCD product wet cake and a mother liquor stream; and
   (c) routing at least a portion of the isolated TMCD product wet cake to a dryer; and
   (d) routing at least a portion of the mother liquor stream to a solvent recovery zone to generate a recycle mother liquor stream and a TMCD reaction by-product impurity rich stream enriched in TMCD reaction by-products, and
   (e) routing at least a portion of the TMCD reaction by-product impurity rich stream enriched with TMCD reaction by-products to purge zone, wherein the product isolation zone comprises a rotary pressure drum filter having a wash ratio from 0.4 to 5.0; wherein said TMCD particles comprise 5% to 45% weight percent solids in the feed slurry; and wherein said feed slurry have a mean particle size ranging from less than 50 microns to about 600 microns.

5. A process for isolating crystallized 2,2,4,4-tetramethyl-1,3-cyclobutanediol (TMCD) particles comprising:
   (a) introducing an isolation feed slurry comprising the TMCD particles and a liquid phase into a product isolation zone;
   (b) removing at least a portion of the liquid phase to thereby produce an isolated TMCD product wet cake and a mother liquor stream; and
   (c) routing at least a portion of the isolated TMCD wet cake to a dryer;
   (d) routing at least a portion of the mother liquor stream to a solvent recovery zone to generate a recycle mother liquor stream and TMCD reaction by-product impurity rich stream enriched in TMCD reaction by products, and
   (e) routing at least a portion of the mother liquor stream to a purge zone, wherein the product isolation zone is defined within a rotary pressure drum filter having a wash ratio from 0.4 to 5.0; wherein said TMCD particles comprise 5% to 45% weight percent solids in the feed slurry; and wherein said feed slurry have a mean particle size ranging from less than 50 microns to about 600 microns.

* * * * *